(12) United States Patent
Leek

(10) Patent No.: US 9,126,036 B2
(45) Date of Patent: Sep. 8, 2015

(54) OPTIONALLY TRANSPORTABLE MACHINE FOR USE IN INTRAOPERATIVE ELECTRON RADIATION THERAPY

(71) Applicant: Paul H. Leek, Willimantic, CT (US)

(72) Inventor: Paul H. Leek, Willimantic, CT (US)

( * ) Notice: Subject to any disclaimer, the term of this patent is extended or adjusted under 35 U.S.C. 154(b) by 0 days.

(21) Appl. No.: 14/212,499

(22) Filed: Mar. 14, 2014

(65) Prior Publication Data

US 2014/0275708 A1 Sep. 18, 2014

Related U.S. Application Data

(60) Provisional application No. 61/787,866, filed on Mar. 15, 2013.

(51) Int. Cl.
| | | |
|---|---|---|
| *A61N 5/01* | (2006.01) | |
| *A61L 2/08* | (2006.01) | |
| *A61N 5/10* | (2006.01) | |

(52) U.S. Cl.
CPC ............. *A61N 5/1077* (2013.01); *A61N 5/1042* (2013.01); *A61N 5/1083* (2013.01); *A61N 2005/1089* (2013.01)

(58) Field of Classification Search
CPC ..... A61N 5/01; A61N 5/1077; A61N 5/1083; A61L 2/08; G21K 5/04
USPC .................................. 250/492.3, 397; 600/1
See application file for complete search history.

(56) References Cited

U.S. PATENT DOCUMENTS

| | | | | |
|---|---|---|---|---|
| 5,317,164 | A * | 5/1994 | Kurokawa | 250/492.3 |
| 5,321,271 | A * | 6/1994 | Schonberg et al. | 250/492.3 |
| 7,183,563 | B2 * | 2/2007 | Avnery | 250/492.3 |
| 2011/0092759 | A1 * | 4/2011 | Koubychine Merkulov et al. | 600/1 |
| 2013/0066135 | A1 * | 3/2013 | Rosa et al. | 600/1 |
| 2014/0275708 | A1 * | 9/2014 | Leek | 600/1 |

FOREIGN PATENT DOCUMENTS

| | | |
|---|---|---|
| EP | 1224953 | 7/2002 |
| EP | 1742519 | 10/2007 |
| WO | WO 2009/050577 | 4/2009 |

* cited by examiner

*Primary Examiner* — David A Vanore

(74) *Attorney, Agent, or Firm* — Holland & Bonzagni, P.C.; Mary R. Bonzagni

(57) ABSTRACT

An electron therapy unit for delivering therapeutic electrons to a patient during an operation that is made up of a movable and stowable beam head that may be connected permanently or temporarily to either a base cabinet or a fixed structure using one or more optionally pivotable arms is provided. In an exemplary embodiment, the inventive electron therapy unit is a mobile unit suitable for in-hospital use or for shared use between hospitals or clinics. The unit is self-contained, small, light and easy to use. It has a very reliable, compact design, allowing for easy stowing to a small rugged configuration for transport. In another exemplary embodiment, the inventive electron therapy unit is a stationary unit. An ion chamber for use with such an optionally transportable electron therapy unit is also provided. The ion chamber employs two or more collector plates and associated bias plates, each having a centrally located hole that extends through the plate. Further provided is a method for reducing or eliminating the possibility of significantly higher current caused by electrical arcs and power excursions during operation of the inventive electron therapy unit.

15 Claims, 14 Drawing Sheets

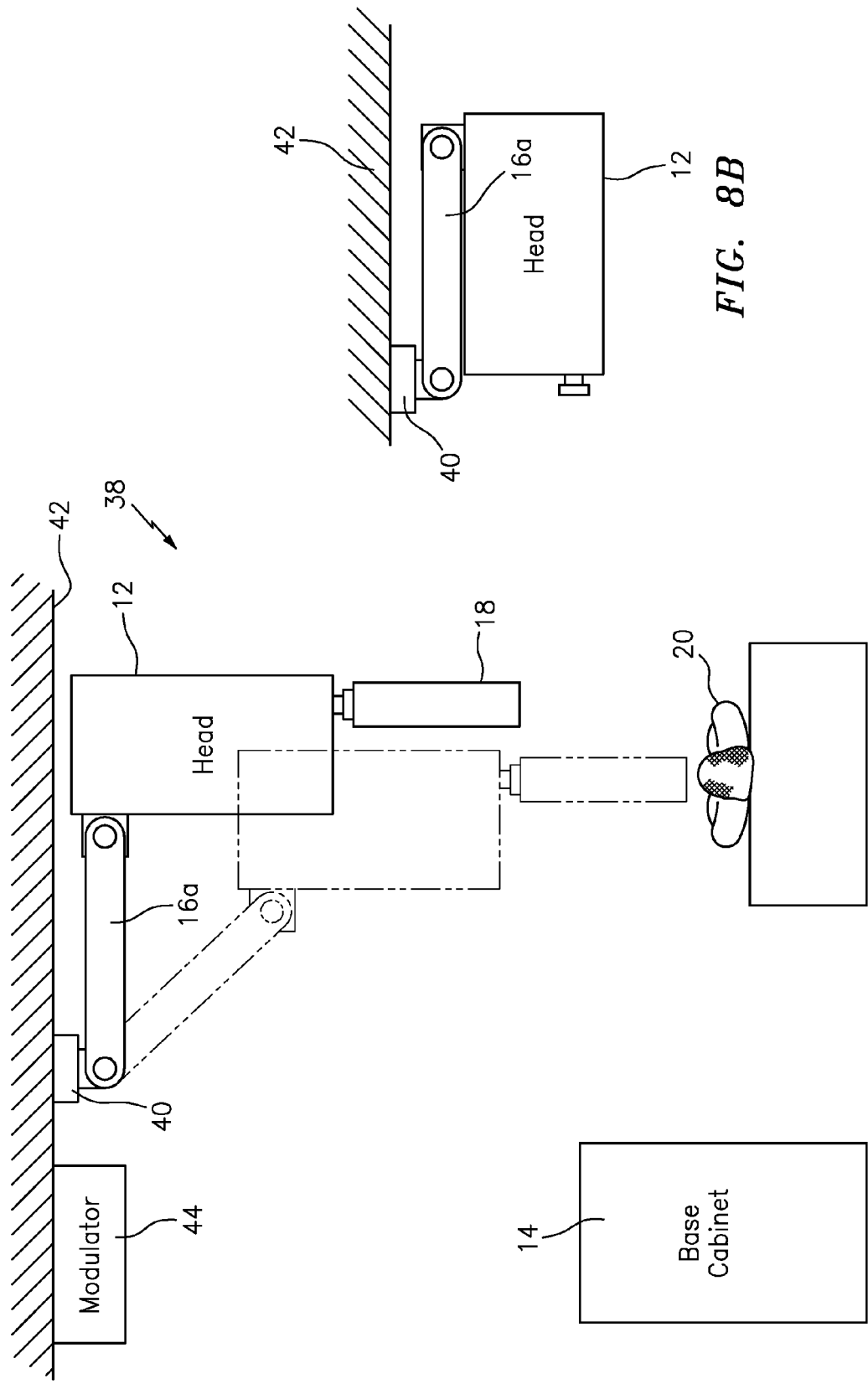

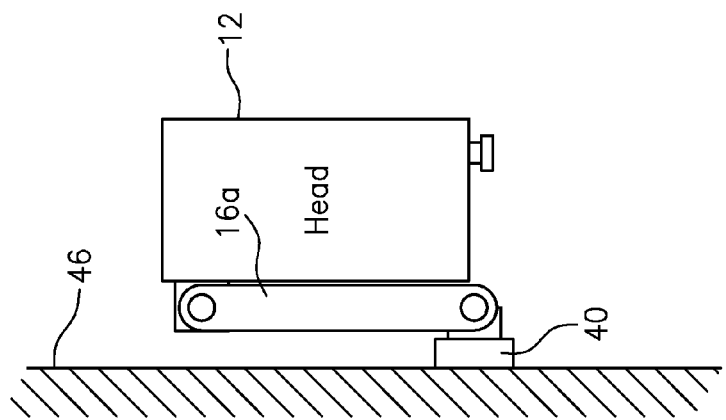
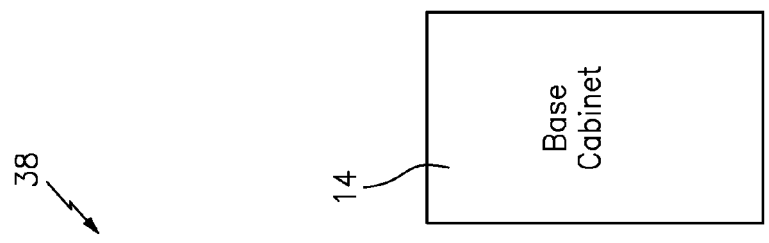
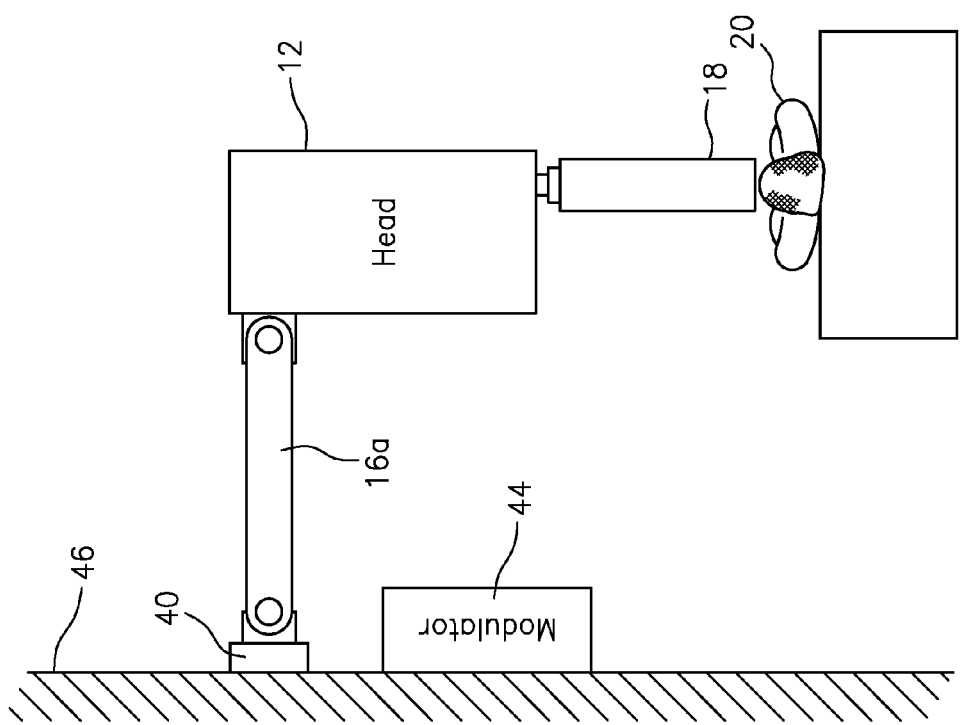
FIG. 9B
FIG. 9A

OPTIONALLY TRANSPORTABLE MACHINE FOR USE IN INTRAOPERATIVE ELECTRON RADIATION THERAPY

RELATED APPLICATION

This application claims priority to U.S. Provisional Patent Application Ser. No. 61/787,866, filed Mar. 15, 2013, which is incorporated herein in its entirety by reference.

TECHNICAL FIELD

The present invention relates to a machine for use in Intra-Operative Electron Radiation Therapy, and more particularly relates to an electron therapy unit for delivering therapeutic electrons to a patient during an operation that is easily stowed and optionally transportable.

BACKGROUND AND SUMMARY OF THE INVENTION

Intra-Operative Electron Radiation Therapy (IOERT) is a treatment by which electron radiation is applied directly to a residual tumor or tumor bed during cancer surgery. Electron beams have been deemed useful for intraoperative radiation treating because, depending on the electron energy, the dose falls off rapidly below a target site, thereby sparing underlying healthy tissue. During IOERT, a physician has direct visualization of the tumor, can exclude normal tissue from the field, and can also protect critical structures within the field and underlying the target volume. IOERT can be administered at the time of surgery when microscopic residual tumor cells are most vulnerable to destruction.

While still in the research stages for breast cancer, IOERT has already become standard treatment for certain types of cancer, such as advanced pelvic and abdominal tumors, sarcoma and colorectal cancers.

Mobetron® radiation therapy machines are used to administer single intraoperative doses of radiation to a patient undergoing tumor excision. To change the effective depth of dose administered by a Mobetron® radiation therapy machine, an operator would change the machine beam energy. A Mobetron® machine reportedly weighs ⅛ the weight of a conventional electron linear accelerator and can be fitted into any operating theater, requiring no room shielding. The physical dimensions and weight of one such Mobetron® machine are as follows: 82 inches in length; 42.7 inches in width; 99.5-111 inches in maximum or operating height; 78 inches in minimum or stowed height; and 2,937 pounds in total weight. For transport, a special jack is used which extends the length of the Mobetron® machine to 95 inches. After a surgical team has completed excision of all visible positive tissue, the Mobetron® machine's applicator is placed within the surgical site as close as possible to the suspected microscopic cancerous tissue to be treated.

The Mobetron® machine has a fixed electron beam head, which moves vertically and can be tilted. This design has limited provision for stowing the head and is relatively large and bulky.

The present invention addresses this drawback by providing an electron therapy unit for delivering therapeutic electrons to a patient during an operation that comprises a movable and stowable beam head that may be connected permanently or temporarily to either (i) a transportable base cabinet, or (ii) a fixed structure, using one or more optionally pivotable arms. The beam head can be moved from a stowed position on either the base cabinet or fixed structure to an operating position over a patient.

In a first exemplary embodiment, the inventive electron therapy unit is a mobile unit suitable for in-hospital use or for shared use between hospitals or clinics where the beam head is connected permanently or temporarily to a transportable base cabinet. The unit is self-contained, small, light and easy to use. It has a very reliable, compact design, allowing for easy stowing to a small rugged configuration for transport.

The inventive unit in this first exemplary embodiment offers size and weight reduction over the Mobetron® machine. In particular, in a preferred embodiment the stowed configuration of the inventive unit has:

- an overall height ranging from about 68 inches to about 95 inches (more preferably, from about 65 inches to about 90 inches);
- an overall width ranging from about 30 inches to about 45 inches (more preferably, from about 30 inches to about 40 inches);
- an overall depth ranging from about 45 inches to about 60 inches (more preferably, from about 46 inches to about 50 inches); and
- a total weight ranging from about 600 pounds to about 800 pounds (more preferably, from about 400 pounds to about 500 pounds).

In a second exemplary embodiment, the inventive electron therapy unit is a stationary unit where the beam head is connected permanently or temporarily to a fixed structure. As will be explained in greater detail below, in this embodiment, the beam head and a modulator are separate from the base cabinet, with the base cabinet containing control electronics, a control computer, and a temperature control unit (TCU).

In a first preferred embodiment, the beam head contains electron beam producing means in the form of a radio-frequency (RF) source and RF components and is attached to either the base cabinet or fixed structure using one or two pivotable arms.

In a second preferred embodiment, the beam head does not contain RF components. Instead, the RF components are contained within the base cabinet and microwave power is carried to the RF source within the beam head through a waveguide in one of the pivotable arms.

In a third preferred embodiment, an arm with a rotating joint is used to connect the beam head to either the base cabinet or fixed structure, while in a fourth preferred embodiment, a rotating joint is used to connect the arm to either (i) the beam head or (ii) the base cabinet or fixed structure, or both (i) and (ii).

In a fifth preferred embodiment, RF components are contained in the base cabinet, and microwave power is carried to the RF source within the beam head through a flexible waveguide.

In a sixth preferred embodiment, the RF source is an RF based linear accelerator, the RF components include an electron gun for producing and delivering a stream of electrons to the linear accelerator, and a direct current (DC) power supply is used for the electron gun. The DC power supply operates at a voltage less than 35 kilovolts, preferably less than or equal to about 5 kilovolts.

The present invention further provides a method for reducing or eliminating the possibility of significantly higher current caused by electrical arcs and power excursions during operation of the inventive electron therapy unit, where the RF source is an RF based linear accelerator, and the RF components include an electron gun for producing and delivering a stream of electrons to the linear accelerator, the method comprising using a DC power supply for the electron gun, the DC power supply operating at a voltage less than 35 kilovolts, preferably less than or equal to about 5 kilovolts.

The present invention further provides an ion chamber for use with an electron therapy unit, and an electron therapy unit that employs such an ion chamber. The ion chamber comprises two or more collector (i.e., signal) plates and associated bias plates, each having a centrally located hole that extends through the plate.

The present invention also provides a method for minimizing electron beam scattering and x-ray generation in an electron therapy unit, the method comprising:

reducing pulse current and pulse repetition rate; and using the ion chamber described above on or within the beam head.

Other features and advantages of the invention will be apparent to one of ordinary skill from the following detailed description and accompanying drawings. Unless otherwise defined, all technical and scientific terms used herein have the same meaning as commonly understood by one of ordinary skill in the art to which this invention belongs. All publications, patent applications, patents and other references mentioned herein are incorporated by reference in their entirety. In case of conflict, the present specification, including definitions, will control. In addition, the materials, methods, and examples are illustrative only and not intended to be limiting.

BRIEF DESCRIPTION OF THE DRAWINGS

The present disclosure may be better understood with reference to the following drawings. Components in the drawings are not necessarily to scale, emphasis instead being placed upon clearly illustrating the principles of the present disclosure.

The drawings depict exemplary embodiments of the present invention in which:

FIG. 1A is a simplified schematic side view of an exemplary embodiment of the mobile electron therapy unit of the present invention (in use) where the beam head contains electron beam producing means and is connected to the base cabinet using two pivotable arms; while

FIG. 2A is a simplified schematic side view of another exemplary embodiment of the inventive mobile unit (in use) where instead of the beam head, the base cabinet contains the RF components; while FIG. 2B is a simplified schematic front view of the embodiment shown in FIG. 2A showing the beam head positioned next to the RF components housed within an upper portion of the base cabinet; while

FIG. 5A is a simplified schematic side view of yet another exemplary embodiment of the inventive mobile unit (in use) where the base cabinet contains the RF components and the microwave power is carried to the RF source in the beam head through a flexible waveguide; while FIG. 5B is a simplified schematic front view of the embodiment shown in FIG. 5A showing the beam head positioned next to the RF components housed within an upper portion of the base cabinet; while

FIG. 6A is a simplified plan view of a prior art ion chamber, while

FIG. 7A is a simplified plan view of an exemplary embodiment of the ion chamber of the present invention, while

FIG. 8A is a simplified side view of an exemplary embodiment of the stationary electron therapy unit of the present invention (in use) where the beam head contains electron beam producing means and where two pivotable arms are used to connect the beam head to a ceiling. In this embodiment, the modulator is also mounted on the ceiling in close proximity to the beam head. In FIG. 8B, a simplified schematic side view of the embodiment shown in FIG. 8A is shown when not in use with the beam head stowed near the ceiling;

FIG. 9A is a simplified side view of another exemplary embodiment of the stationary unit of the present invention (in use) where two pivotable arms are used to connect the beam head to a wall or post. Here, the modulator is also mounted on the wall or post in close proximity to the beam head. In FIG. 9B, a simplified schematic side view of the embodiment shown in FIG. 9A is shown when not in use with the beam head stowed near the wall or post;

DETAILED DESCRIPTION OF THE INVENTION

While the electron therapy unit of the present invention will be described herein mainly in the treatment of breast cancer, it is not so limited. Other superficial treatments using electrons are possible. Examples include, but are not limited to, advanced pelvic and abdominal tumors, sarcoma and colorectal cancers.

Figure 1A:
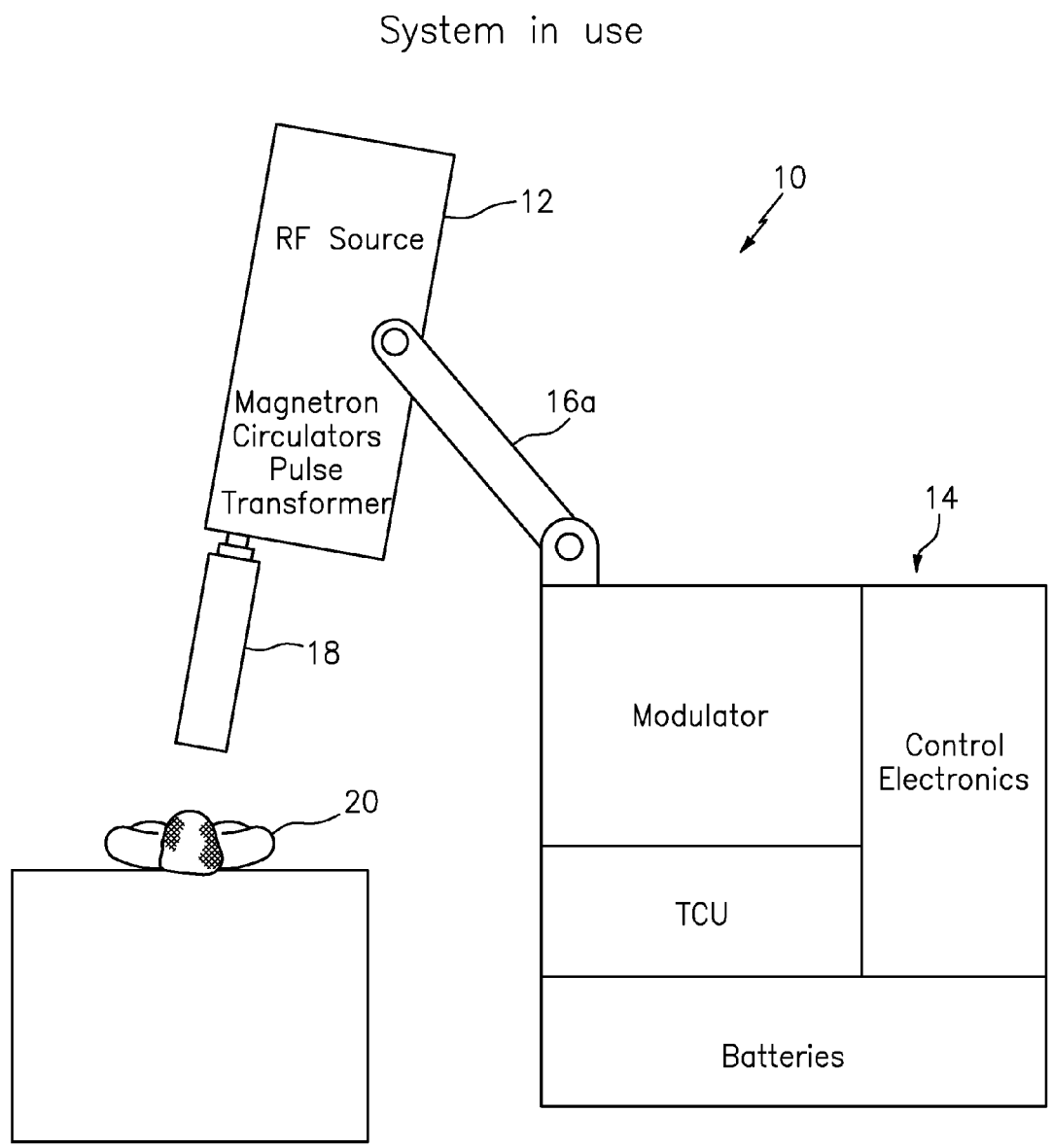

Referring now to the drawings in detail, an exemplary embodiment of the mobile electron therapy unit of the present invention is shown in FIG. 1A, marked with reference numeral 10. The electron therapy unit 10 is made up of a movable and stowable beam head 12 connected to a base cabinet 14 using two pivotable arms 16a and 16b (not shown) (e.g., GD60 suspension system available from MAVIG GmbH, Munich, Germany). The beam head 12, which employs a beam nozzle 18, contains electron beam producing means in the form of a radio-frequency (RF) source (e.g., an RF based linear accelerator or linac) and RF components (e.g., a magnetron, electron gun, circulators, resistors, isolation transformers). The base cabinet 14, in this exemplary embodiment, contains a modulator, a power management system, control electronics, a control computer, a TCU, and necessary drive motors and gears. It is noted that this exemplary embodiment may also be made with only one arm.

In operation, an electron beam, which is generated in beam head 12, is directed along beam nozzle 18 toward a patient 20 for the purpose of treating, for example, breast cancer. As alluded to above, electron beams are useful for treating breast cancer because the maximum of dose deposition occurs near the surface. The dose then decreases rapidly with depth, sparing underlying tissue. Electron beams usually have nominal energies in the range 4-25 MeV, which (depending on the energy) translates to a treatment range of approximately 1-13 cm (in water-equivalent tissue). Although the X-ray target is removed in electron mode, the beam may be fanned out by sets of thin scattering foils in order to achieve flat and symmetric dose profiles in the treated tissue.

Figure 6A:
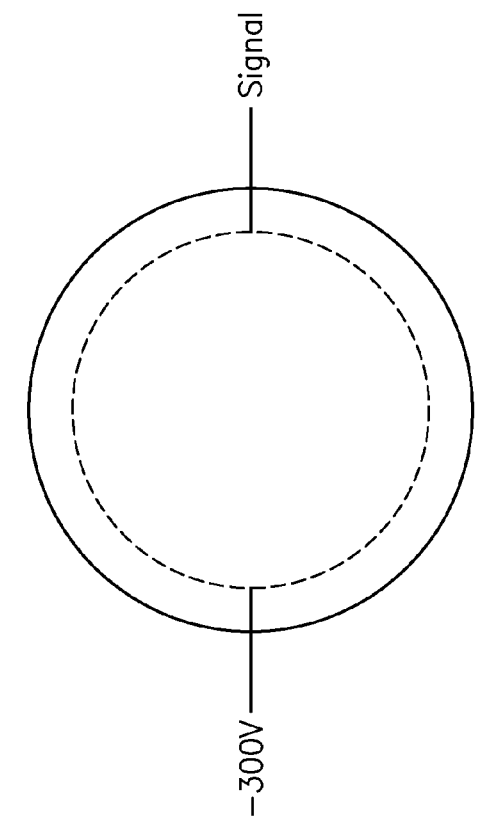
Figure 6B:
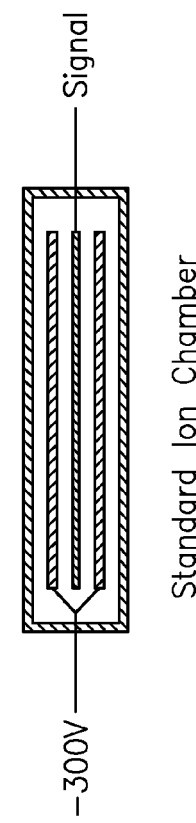
FIG. 6B is a simplified cutaway side view of the prior art ion chamber shown in FIG. 6A.

When the electron beam exits the beam head 12 through a window (e.g., 25 micron Titanium window) in the beam head, an ion chamber measures the exposure rate (dose rate). As best shown in FIGS. 6A and 6B, an ion chamber is typically made up of two thin aluminum plates with a net voltage (in this example) of −300 volts with another plate between them. This third plate (i.e., collector or signal plate) measures the ions generated by the electron beam, not the actual electrons.

Figure 7A:
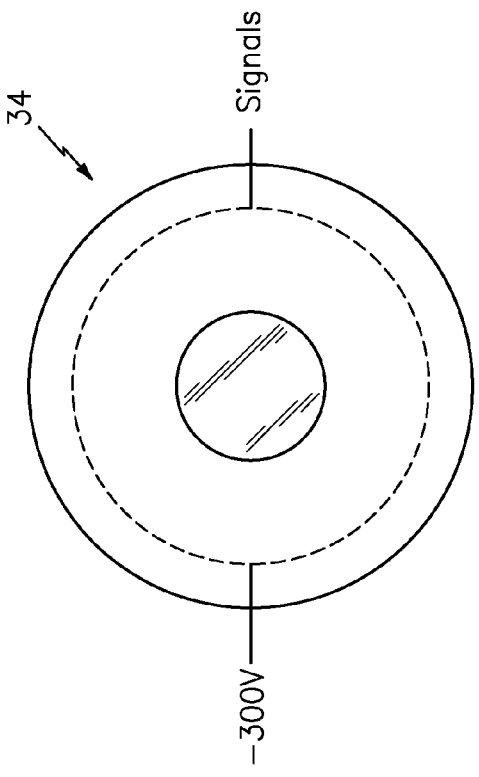
Figure 7B:
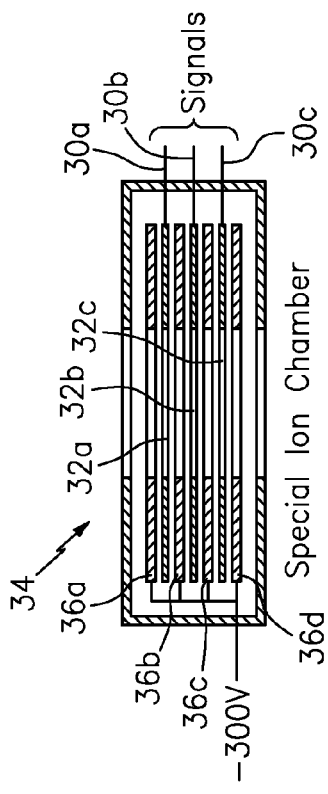
FIG. 7B is a simplified cutaway side view of the exemplary embodiment of the inventive ion chamber shown in FIG. 7A.

In the present invention, an object is to avoid or reduce possible scattering of the beam, while another object is to reduce the generation of X-rays. Although X-rays are not being used, X-ray generation is inherent in stopping high energy electrons. As will be readily appreciated by those skilled in the art, where the inventive mobile or stationary electron therapy unit is intended for use in an operating theater with no radiation shielding, there is a need to keep incidental X-ray generation to a minimum. These objects are accomplished in two ways. First, the electron beam average intensity is reduced by from about 300 to about 1000 times and the materials that the beam hits is controlled. As a result, the pulse repetition rate ranges from about 2 to about 10 pulses per second (PPS) and the pulse current ranges from about 2 to about 10 milliamps. Second, and as best shown in FIGS. 7A and 7B, three collector or signal plates 30a-c, oriented perpendicular to the beam direction, each having a centrally located hole 32a-c, extending through the plate (i.e., washers), are used in inventive ion chamber 34. Each collector plate 30 is separated from other collector plates by bias plates 36a-d, which also have a centrally located hole extending there through. While at least two collector or signal plates are required to avoid over exposure, three signal plates are used in this exemplary embodiment to provide a continuous check on ion chamber accuracy. Ion chamber 34 serves to reduce the X-ray contamination caused by the beam passing through the ion chamber plates.

Figure 1B:
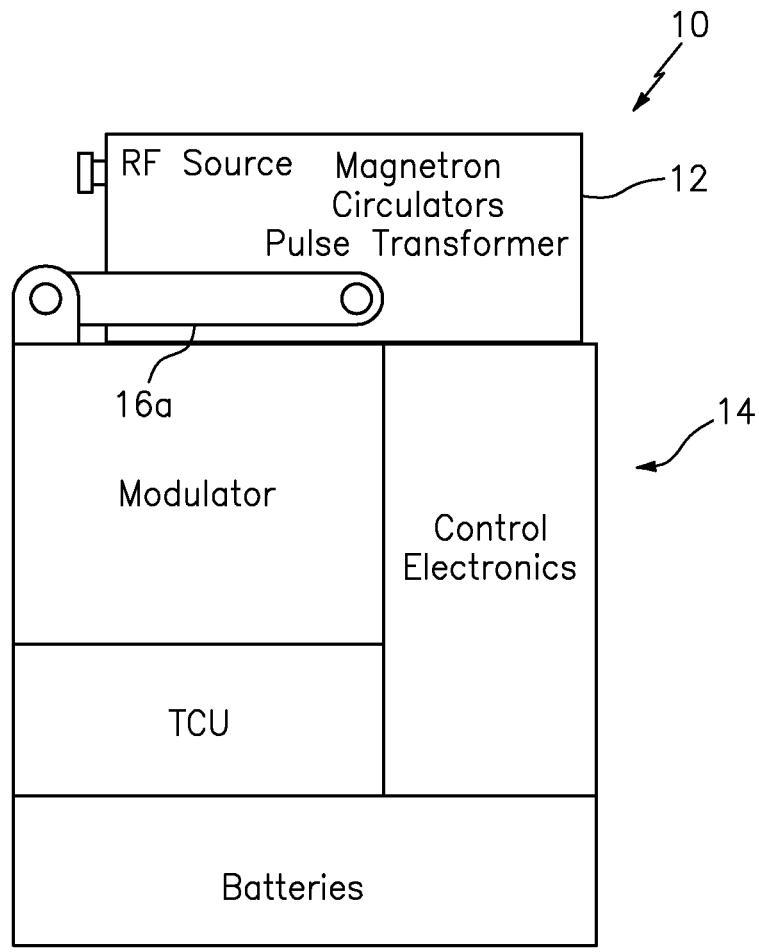
FIG. 1B is a simplified schematic side view of the embodiment shown in FIG. 1A when not in use with the beam head stowed on top of the base cabinet.

As best shown in FIG. 1B, upon completion of the prescribed treatment, and after the beam nozzle 18 is removed from the beam head 12, the beam head 12 is moved back onto the base cabinet 14 and covered for transport and storage.

The beam nozzle 18 is attached to the beam head 12 only during use or treatment, is made of a substantially transparent material treated to be semi-conductive, and is capable of being sterilized. The beam nozzle 18, which may be of a unitary or multi-part construction, has a number of sizes including those measuring from about 2 inches up to about 4 inches in diameter in about 1 inch increments or steps.

In one exemplary embodiment, the beam nozzle 18 is made up of two parts, a first upper part that attaches directly to the beam head 12, and an adjustable, sterilizable second or lower part that slides on and over the surface of the first part to provide an adjustable joint that will not put pressure on a patient's body. An interlock is provided on the beam nozzle 18 to ensure that the nozzle never presses on the patient's body. In this exemplary embodiment, the nozzle pair is 18 inches long when fully extended and 12 inches long when collapsed. The second or lower part of the beam nozzle 18 is closed off at the patient end by a thin transparent window, with both the lower part and the thin transparent window capable of being sterilized. In use, the lower part will have a sterile plastic bag to enclose it.

The inventive electron therapy unit 10 is designed to fit through a standard door opening and to be maneuvered by two radiation technicians. The inventive unit may be provided with means for motorized movement.

The linear particle accelerators or linacs used in the practice of the present invention generate high energy electrons for medicinal purposes. These so-called medical linacs produce electrons with an energy range from 4 MeV up to around 25 MeV. The shape and intensity of the beam produced by a medical linac may be modified or collimated by a variety of means.

Preferred medical linacs include 10 MeV electron beam systems, which have a very low duty cycle and low current to provide several hundred Rads per minute of electron beam. These preferred linacs are capable of variable electron beam energy to vary the depth of tissue radiated. As noted above, electrons have limited penetration in tissue, from about 1.75 to about 2 inches for 10 MeV.

Also included among the preferred medical linacs are multi-energy systems, which allow the user to choose a suitable energy up to 10 MeV for treatment.

While the machine beam energy of these medical linacs could be changed to alter the effective depth of dose, in a preferred embodiment, layers of tissue equivalent material called bolus are used to effectively change the depth at which the dose ends. Shapes and tapered material are also used to provide a tapered penetration, if necessary. By way of such an approach, a bolus is designed based on a CT scan taken during a patient workup. As will be readily appreciated by those skilled in the art, the ability to achieve precise targeting at the time of treatment delivery is dependent upon accurate patient setup and reproducibility of the geometry and radiological path length.

The RF components in the exemplary embodiment mentioned above include a magnetron, an electron gun, one or more circulators to shunt power, one or more resisters for applying a resistor-divided voltage to electrode elements provided in the electron gun circuit, and one or isolation transformers to drive the electron gun. High power sources of microwaves such as klystrons and magnetrons serve as the driving force for modern particle accelerators. A magnetron, due to its smaller size, is preferably used as the driving force for the medical linac in the inventive electron therapy unit. In this exemplary embodiment, the gun pulse current is less than 10 milliamps. In order to reduce or eliminate the possibility of significantly higher current in the event of an electrical arc, the gun high voltage is fed from the magnetron cathode through a large high resistance (e.g., at least 100,000 ohms). This limits the gun current to 20 milliamps.

In another exemplary embodiment, the possibility of significantly higher current is eliminated by the use of a DC power supply for the electron gun.

As alluded to above, the electron gun used on an electron beam accelerator is operated at a very low beam current as the ionizing effectiveness of an electron beam is much higher than an x-ray beam. In consequence this current must be tightly controlled, where unexpected high currents during treatment could prove fatal to a patient. In a preferred embodiment of the present invention, unexpected high currents are avoided by using a separate DC power supply for the electron gun, which operates at a much lower voltage. This allows the beam current to be monitored continuously. Using a much lower voltage, instead of the normal 35 kilovolts (kV), reduces the chance of excessive emitted current.

This preferred embodiment needs a very low current (i.e., a few milliamps of beam current). So using a DC power supply even at several kilovolts uses only a few watts. Tests have shown that a gun drive voltage of as low as 2.5 kV with a specially graduated accelerating cavity design accepts about 20 percent (20%) of gun current. So for an electron beam of 2 to 10 milliamps, which is typical, the gun current required is 10 to 50 milliamps. A gun drive supply at 5 kV and 50 milliamps is only 250 watts. This power supply operates continuously during operation. It can be switched on and off in tandem with the modulator to reduce power loss, but the supply does not need to be pulsed. This allows a control system to easily monitor the gun voltage and current. By operating at a stable, low voltage the gun can be isolated from the arcs and power excursions that occur in the magnetron circuit. This makes the gun emission very stable and reproducible.

Figure 10:
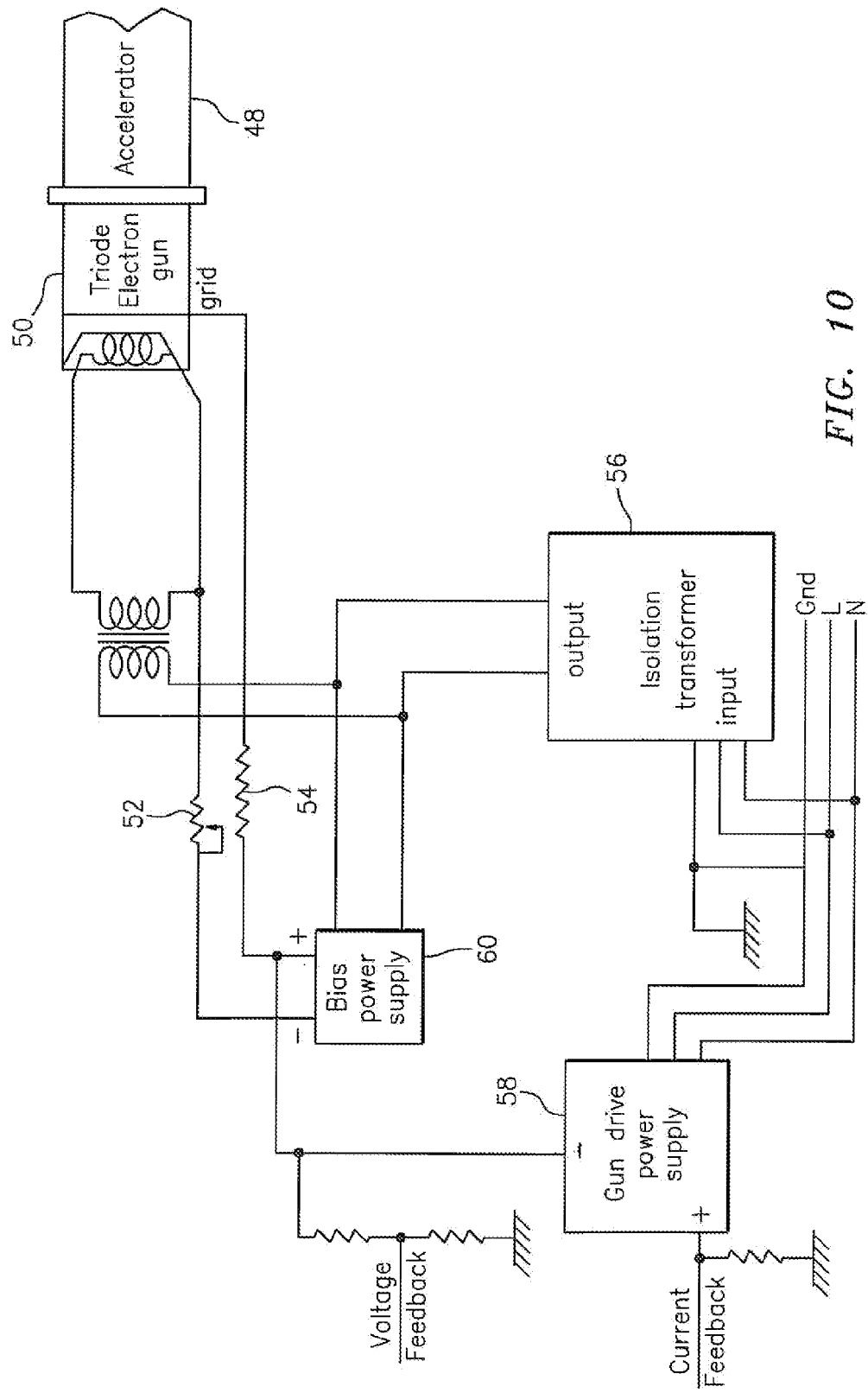
FIG. 10 is a simplified schematic plan view of a preferred embodiment of the inventive electron therapy unit, where the RF source is an RF based linear accelerator, the RF components include an electron gun for producing and delivering a stream of electrons to the linear accelerator, and a DC power supply is used for the electron gun.

As best shown in FIG. 10, electron beam producing means in the form of an RF based linear accelerator or linac 48 and RF components, namely, a magnetron (not shown), electron gun 50, resistors 52, 54, isolation transformers 56, serve to generate a very low electron beam current of from about 2 to about 10 milliamps. In this preferred embodiment, the gun drive power supply 58 can be anything up to several kilovolts, 5 kV can be considered typical. The gun bias supply 60 is a few volts. This can be a positive or negative bias depending on the gun characteristics and the gun drive voltage chosen. The inventive electron therapy unit has been tested with a gun drive of 2.5 kV and bias supply at 50 volts. The standing gun current is limited to 10 milliamps by the gun drive power supply and the cathode resistors 52, 54.

As noted above, the base cabinet 14 contains all remaining components necessary for the operation of the inventive electron therapy unit 10. In an exemplary embodiment, base cabinet 14 contains a modulator, a power management system, batteries, control electronics, a control computer, a temperature control unit (TCU), and necessary drive motors and gears. The modulator is a small commercial unit that uses solid state switches to provide DC pulses to the magnetron. The power management system uses a combined battery charger and power inverter. The control electronics uses a programmable logic controller (PLC) with a touch screen computer. The control computer is a small laptop or similar unit that is kept in a storage box in base cabinet 14 along with a control panel with on and off buttons, a key-switch and an emergency off button. The storage box may also house a standard set of beam nozzles or applicators (e.g., four (4) applicators). The control computer is attached to the PLC by wire. As will be readily appreciated by those skilled in the art, wireless (e.g., Bluetooth) connections are preferably not used so as to ensure that no extraneous signal can operate the machine. The TCU used in this exemplary embodiment is a small water cooler/heater.

Figure 2A:
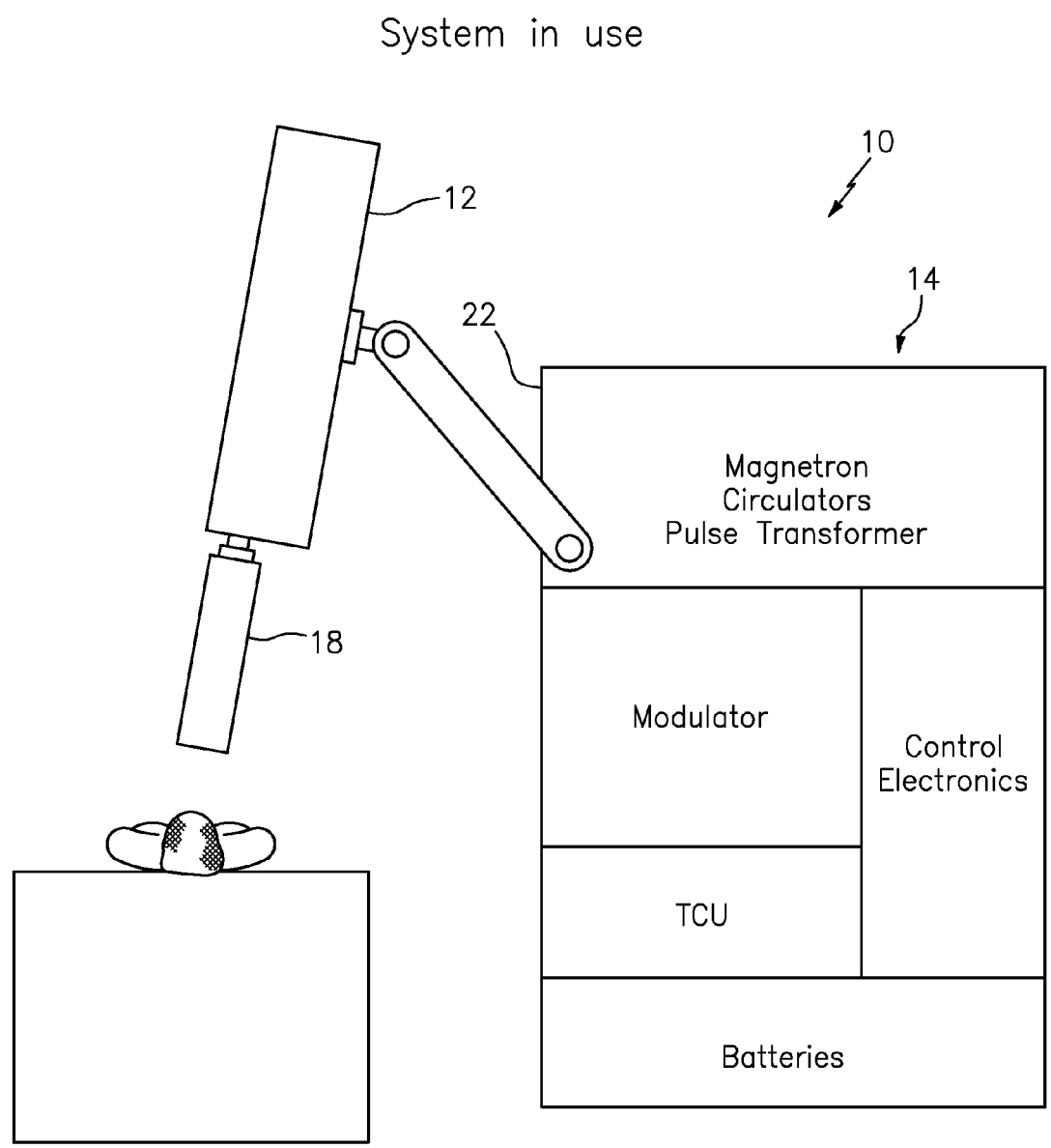
Figure 2B:
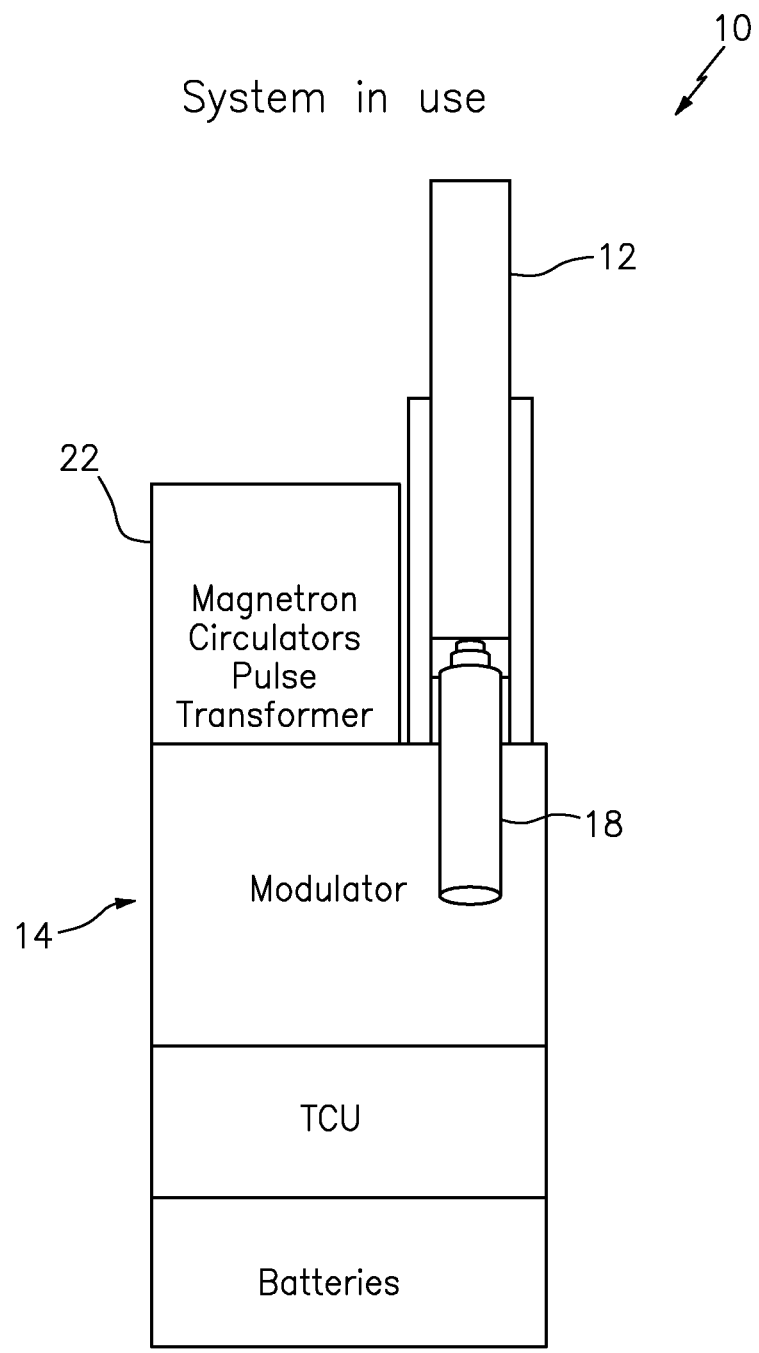
Figure 2C:
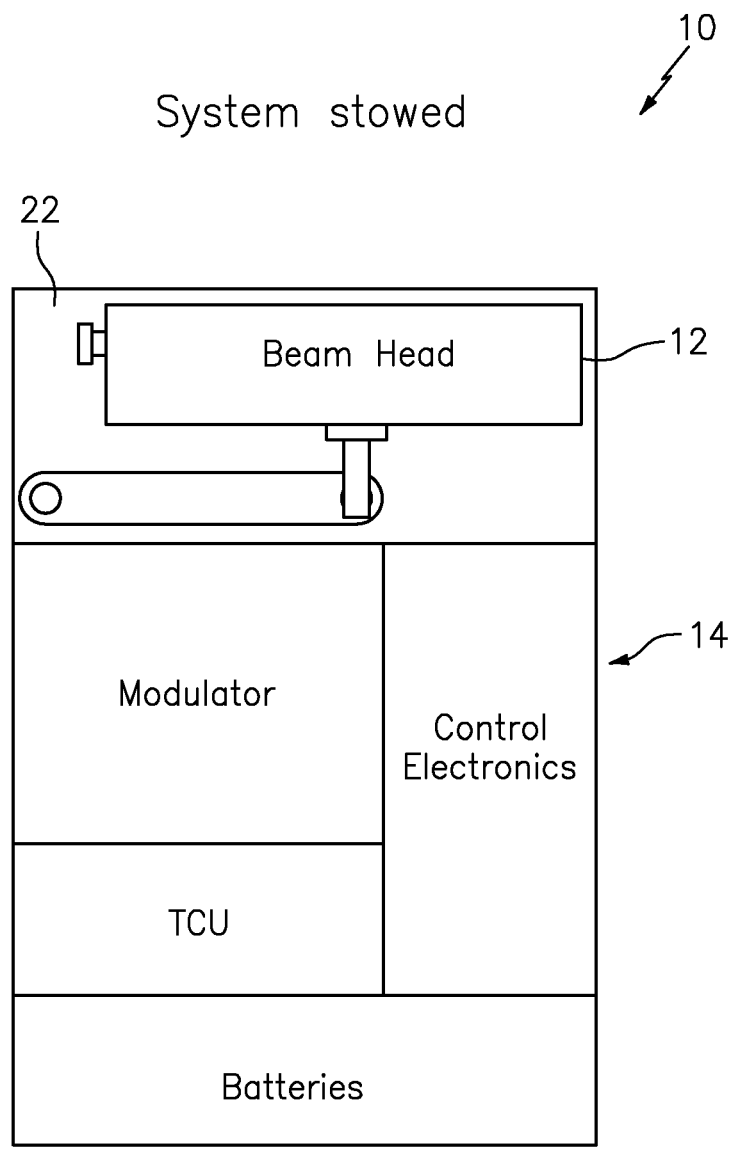
FIG. 2C is a simplified schematic side view of the embodiment shown in FIGS. 2A and 2B when not in use with the beam head stowed next to the upper portion of the base cabinet housing the RF components.

A second exemplary embodiment of the invention is shown in FIGS. 2A-2C. In this embodiment, the beam head 12 does not contain the RF components. Instead, and as best shown in FIG. 2B, the RF components are contained in an upper portion 22 of the base cabinet 14, with the beam head 12 conveniently positioned next to this upper portion 22 of the base cabinet 14. In this second exemplary embodiment, microwave power is carried to the head 12 through a first waveguide rotating joint (not shown) located in one of the arms, with a second waveguide rotating joint (also not shown) used to connect the waveguide to the beam head 12. This arrangement allows for a much smaller and lighter beam head. This exemplary embodiment may also be made with only one arm.

As best shown in FIG. 2C, upon completion of the prescribed treatment, and after the beam nozzle 18 is removed from the beam head 12, the beam head 12 is moved back onto the base cabinet 14 next to the upper portion 22 and then covered for transport and storage. The beam nozzle 18 may be stowed in, for example, an accessory box in base cabinet 14.

Figure 3:
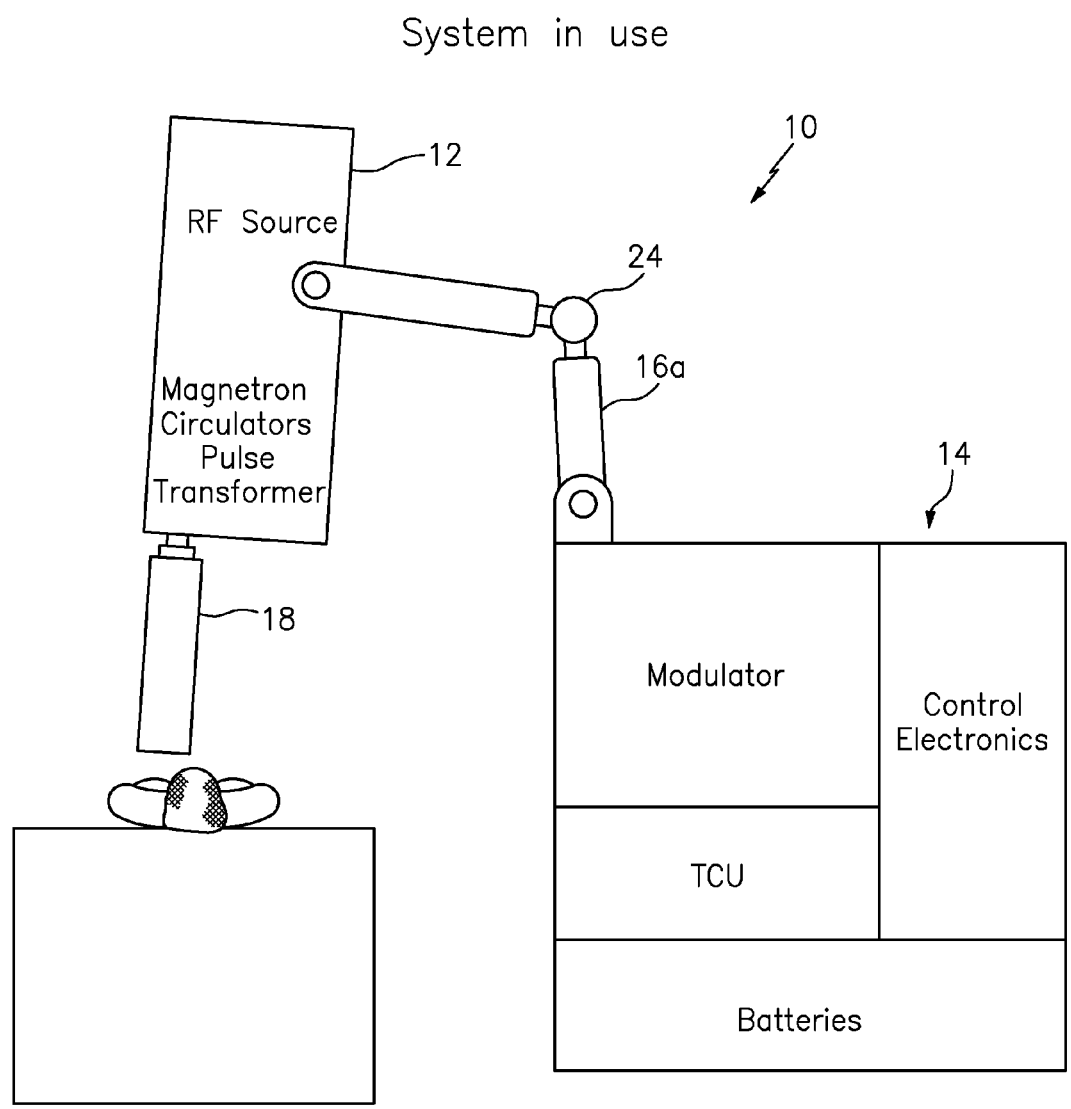
FIG. 3 is a simplified schematic side view of yet another exemplary embodiment of the inventive mobile unit (in use) where a rotating joint is used in the arm(s) connecting the beam head to the base cabinet.

In a third exemplary embodiment, which is best shown in FIG. 3, a rotating joint 24 is used in the arms 16a and 16b (not shown). As will be readily appreciated by those skilled in the art, using two arms allows more flexibility in the positioning of the head. When stored, both arms can be folded, thus allowing for the use of longer length arms.

Figure 4:
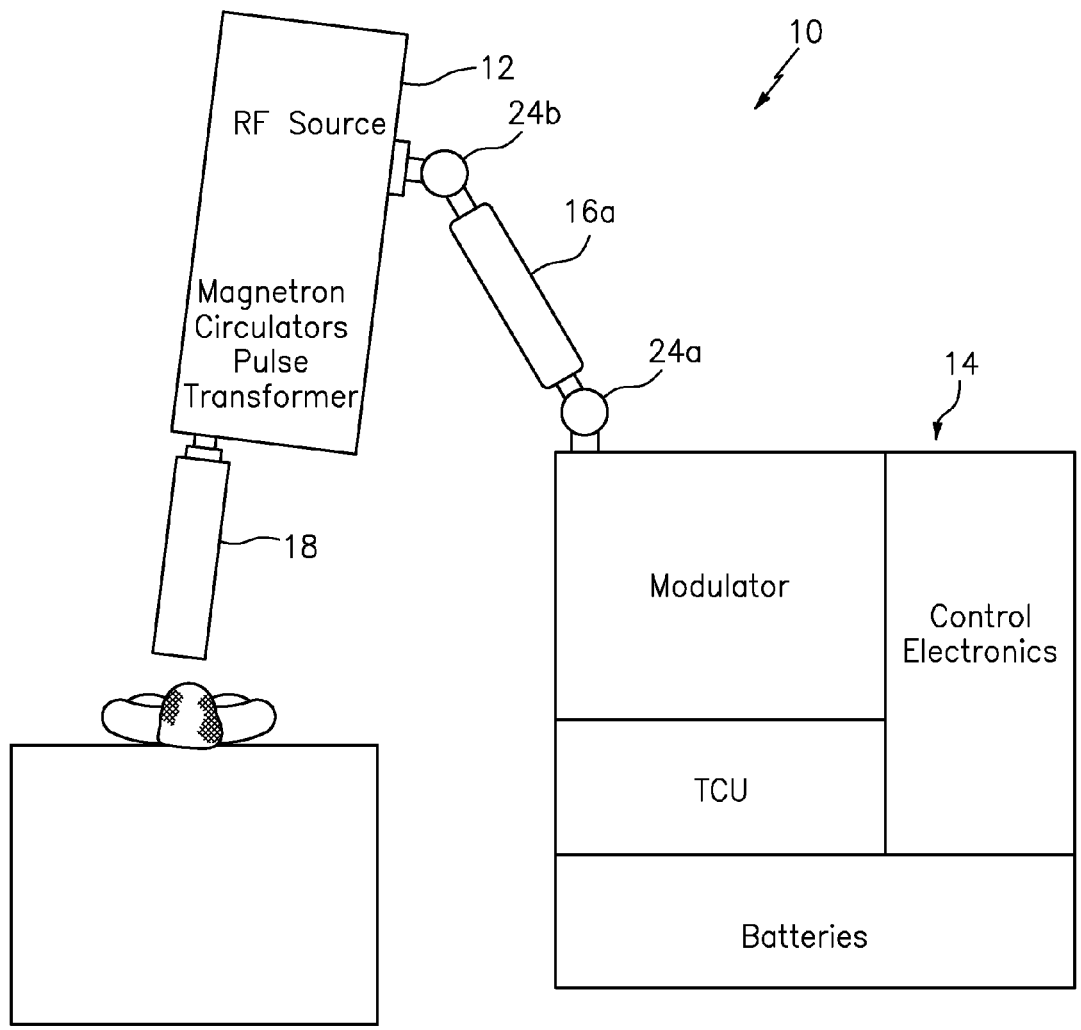
FIG. 4 is a simplified schematic side view of yet another exemplary embodiment of the inventive mobile unit (in use) where a rotating joint is used on both the beam head and the base cabinet.

A fourth exemplary embodiment is shown in FIG. 4. In this embodiment, rotating joints 24a-b, 24c-d (not shown), are used to attach the arms 16a and 16b (not shown) to the beam head 12 and the base cabinet 14. Again, this allows for more flexibility in the use of the inventive system.

Figure 5A:
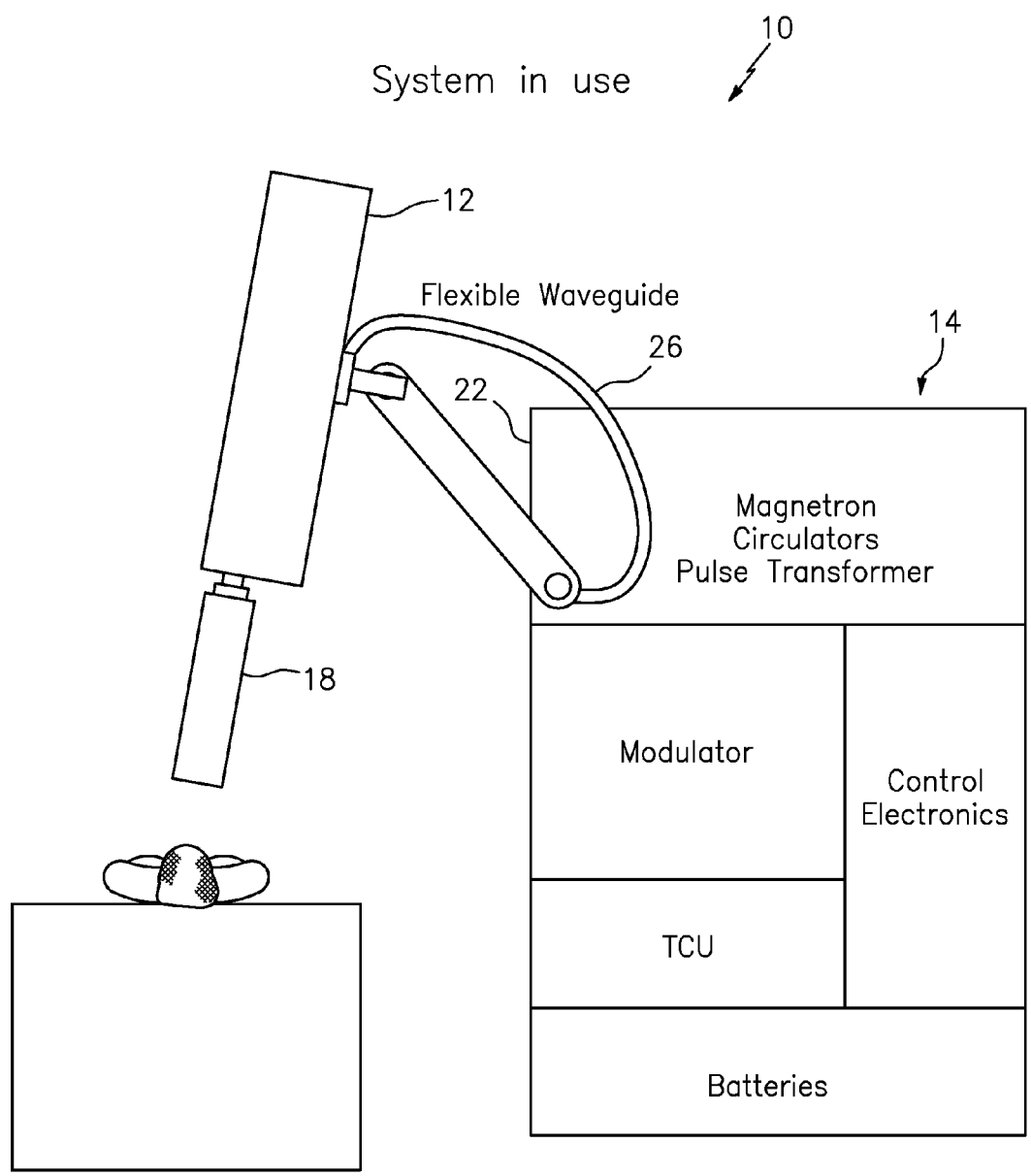
Figure 5B:
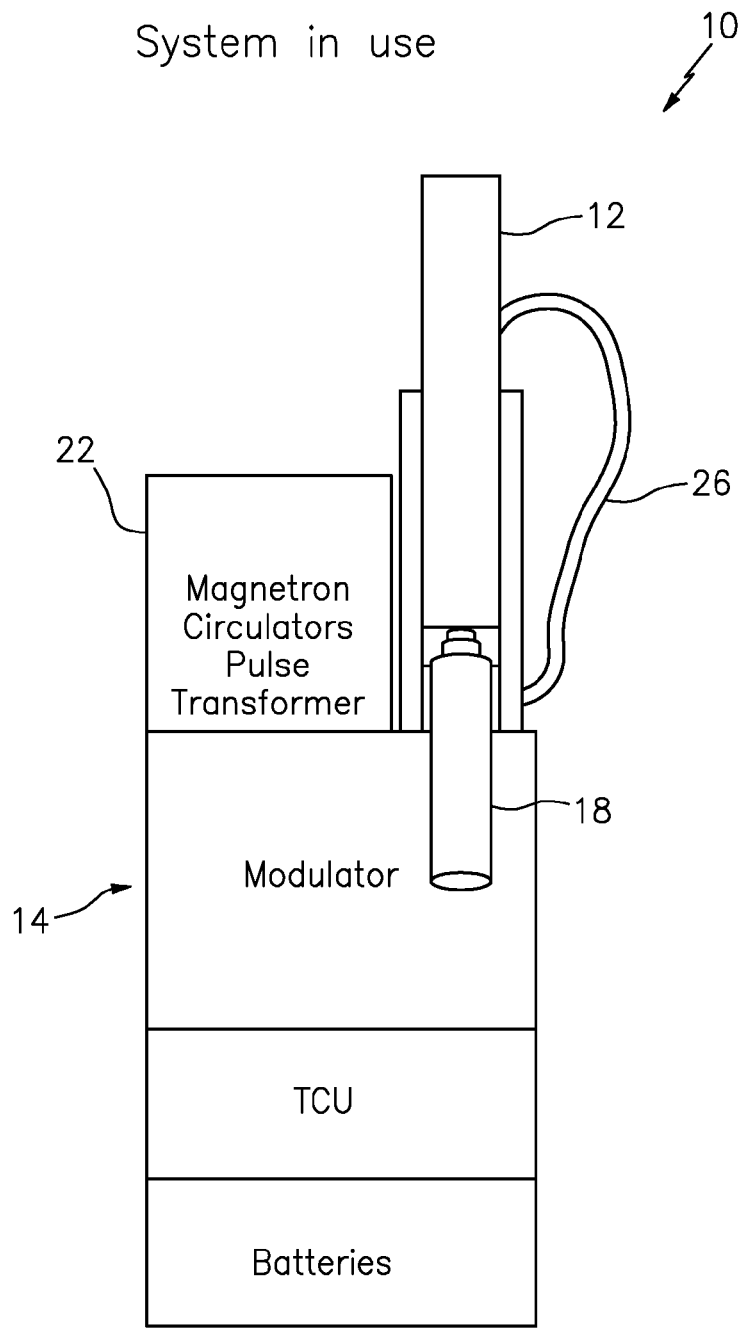
Figure 5C:
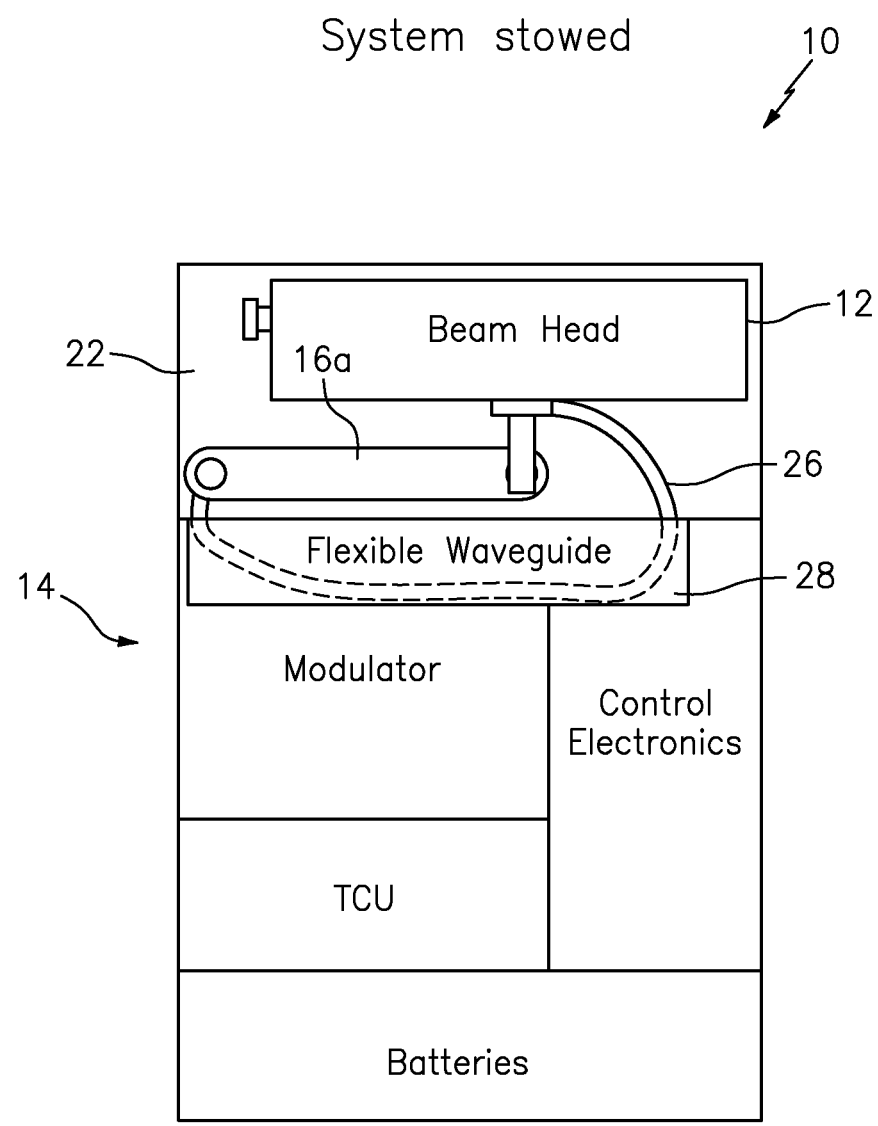
FIG. 5C is a simplified schematic side view of the embodiment shown in FIGS. 5A and 5B when not in use with the beam head and flexible waveguide stowed next to the upper portion of the base cabinet housing the RF components.

In a fifth exemplary embodiment, which is shown in FIGS. 5A-5C, the RF components are contained in the upper portion 22 of the base cabinet 14, instead of in beam head 12, and the beam head 12 is conveniently positioned next to this upper portion 22 of the base cabinet 14 (see FIG. 5B). In this exemplary embodiment, microwave power is carried to the head 12 through a flexible waveguide 26. This arrangement also allows for a much smaller and lighter beam head. This exemplary embodiment may also be made with only one arm.

As best shown in FIG. 5C, upon completion of the prescribed treatment, and after the beam nozzle 18 is removed from the beam head 12, the beam head 12 with attached flexible waveguide is moved back onto the base cabinet 14 and an underlying compartment 28, and next to the upper portion 22 and then covered for transport and storage. The beam nozzle 18 may be stowed in, for example, an accessory box in base cabinet 14.

An exemplary embodiment of the stationary electron therapy unit of the present invention is shown in FIG. 8A, marked with reference numeral 38. The electron therapy unit 38 is made up of the movable and stowable beam head 12 connected (temporarily or permanently) using two pivotable arms 16a and 16b (not shown) and anchoring member 40 to a ceiling 42. It is noted that this exemplary embodiment may also be made with only one arm.

The beam head 12, which employs a beam nozzle 18, contains electron beam producing means in the form of an RF source and RF components. A modulator 44 is also mounted onto the ceiling 42 in close proximity to the beam head 12. The base cabinet 14, in this exemplary embodiment, is smaller in size and contains control electronics, a control computer, and a TCU. The base cabinet may be movable or stationary. A power management system, which uses a combined battery charger and power inverter, as well as batteries are not needed for the stationary embodiment, which can be driven directly from, for example, a 120 volt main power supply, the current being less than 12 amps.

As best shown in FIG. 8B, upon completion of the prescribed treatment, and after the beam nozzle 18 is removed from the beam head 12, the beam head 12 is moved back toward the ceiling 42 for storage.

Another exemplary embodiment of the stationary electron therapy unit of the present invention is shown in FIG. 9A. In this embodiment, two pivotable arms 16a and 16b (not shown) and anchoring member 40 are used to connect the beam head to a wall or post 46. Modulator 44 is also mounted on the wall or post 46. Upon completion of the prescribed treatment and after the beam nozzle is removed from the beam head, the beam head is moved back toward the wall or post 46 for storage.

While various embodiments of the present invention have been described above, it should be understood that they have been presented by way of example only, and not limitation. For example, in the mobile unit embodiment, beam head 12 may be mounted (manually or otherwise) on a separate stand instead of on base cabinet 14. Thus, the breadth and scope of the present invention should not be limited by any of the exemplary embodiments.

I claim:

1. An electron therapy unit for delivering therapeutic electrons to a patient during an operation that comprises a movable and stowable beam head that may be connected permanently or temporarily to either (i) a transportable base cabinet, or (ii) a fixed structure, using one or more optionally pivotable arms, wherein the beam head can be moved from a stowed position on either the base cabinet or fixed structure to an operating position over a patient.

2. The electron therapy unit of claim 1, wherein the unit is a mobile unit where the beam head is connected permanently or temporarily to a transportable base cabinet.

3. The mobile electron therapy unit of claim 2, wherein when the unit is stowed, it has:
   an overall height ranging from about 68 inches to about 95 inches;
   an overall width ranging from about 30 inches to about 45 inches;
   an overall depth ranging from about 45 inches to about 60 inches; and
   a total weight ranging from about 600 pounds to about 800 pounds.

4. The mobile electron therapy unit of claim 3, wherein when the unit is stowed, it has:
   an overall height ranging from about 65 inches to about 90 inches;
   an overall width ranging from about 30 inches to about 40 inches;
   an overall depth ranging from about 46 inches to about 50 inches; and
   a total weight ranging from about 400 pounds to about 500 pounds.

5. The electron therapy unit of claim 1, wherein the unit is a stationary unit where the beam head is connected permanently or temporarily to a fixed structure.

6. The electron therapy unit of claim 1, wherein
   the beam head contains electron beam producing means in the form of a radio-frequency source and radio-frequency components; or
   the beam head contains a radio-frequency source, the base cabinet contains radio-frequency components, and microwave power is carried to the radio-frequency source within the beam head through a waveguide in one of the optionally pivotable arms;
   the one or more optionally pivotable arms is one or more arms with a rotating joint;
   a rotating joint is used to connect the one or more optionally pivotable arms to either the beam head or the base cabinet, or both; or
   the beam head contains a radio-frequency source, the base cabinet contains radio-frequency components, and microwave power is carried to the radio-frequency source within the beam head through a flexible waveguide.

7. The electron therapy unit of claim 1, wherein a beam nozzle is attached to the beam head during use and treatment, wherein the beam nozzle is made up of two parts, a first upper part that attaches directly to the beam head, and an adjustable, sterilizable second or lower part that slides on and over the surface of the first part to provide an adjustable joint that will not put pressure on a patient's body.

8. The electron therapy unit of claim 7, wherein an interlock is provided on the beam nozzle to ensure that the nozzle never presses on the patient's body.

9. The electron therapy unit of claim 7, wherein the second or lower part of the beam nozzle is closed off at one end facing the patient by a thin transparent window, with both the lower part and the thin transparent window capable of being sterilized.

10. The electron therapy unit of claim 6, wherein the radio-frequency source is a radio-frequency based linear accelerator, wherein the radio-frequency components include an electron gun for producing and delivering a stream of electrons to the linear accelerator, and wherein a direct current power supply is used for the electron gun.

11. The electron therapy unit of claim 10, wherein the direct current power supply operates at a voltage less than 35 kilovolts.

12. The electron therapy unit of claim 11, wherein the direct current power supply operates at a voltage less than or equal to about 5 kilovolts.

13. A method for reducing or eliminating the possibility of significantly higher current caused by electrical arcs and power excursions during operation of the electron therapy unit of claim 6, wherein the radio-frequency source is a radio-frequency based linear accelerator, wherein the radio-frequency components include an electron gun for producing and delivering a stream of electrons to the linear accelerator, wherein the method comprises using a direct current power supply for the electron gun, the direct current power supply operating at a voltage less than 35 kilovolts.

14. The method of claim 13, wherein the direct current power supply operates at a voltage less than or equal to about 5 kilovolts.

15. The electron therapy unit of claim 1, which further comprises an ion chamber for measuring electron beam energy exiting the beam head, wherein the ion chamber comprises two or more collector plates and associated bias plates, each having a centrally located hole that extends through the plate.

* * * * *